United States Patent [19]

Talcott

[11] Patent Number: 4,558,112

[45] Date of Patent: Dec. 10, 1985

[54] LOW OILING GEL FILLED ARTICLES, SILOXANE GELS AND LIQUIDS THEREFOR, AND METHODS FOR PRODUCING SAME

[75] Inventor: Thomas D. Talcott, Irvine, Calif.

[73] Assignee: Boehringer Mannheim Corporation, Indianapolis, Ind.

[21] Appl. No.: 270,867

[22] Filed: Jun. 5, 1981

[51] Int. Cl.$^4$ ............................................. C08G 77/12
[52] U.S. Cl. ..................................... 528/31; 528/15; 528/32; 528/10; 556/479
[58] Field of Search ................... 556/479; 528/15, 31, 528/32, 10

[56] References Cited

U.S. PATENT DOCUMENTS

| | | | |
|---|---|---|---|
| Re. 26,697 | 10/1969 | McVannel | 528/14 |
| 2,634,284 | 4/1953 | Hyde | 528/21 |
| 2,970,150 | 1/1961 | Bailey | 528/32 |
| 2,979,519 | 4/1961 | Pierce et al. | 528/14 |
| 3,020,260 | 2/1962 | Nelson | 528/15 |
| 3,037,962 | 6/1962 | Hartung et al. | 528/21 |
| 3,159,662 | 12/1964 | Ashby | 528/15 |
| 3,183,209 | 5/1965 | Hartung et al. | 528/32 |
| 3,293,663 | 12/1966 | Cronin | 3/36 |
| 3,294,740 | 12/1966 | McVannel | 528/14 |
| 3,296,291 | 1/1967 | Chalk | 556/479 |
| 3,337,497 | 8/1967 | Bostick | 528/12 |
| 3,652,711 | 3/1972 | Triem et al. | 528/14 |
| 3,681,787 | 8/1972 | Perras | 3/36 |
| 4,100,627 | 7/1978 | Brill, III | 528/10 |
| 4,138,382 | 2/1979 | Polmanteer | 528/32 |

*Primary Examiner*—Melvyn I. Marquis
*Attorney, Agent, or Firm*—Woodard, Weikart, Emhardt & Naughton

[57] ABSTRACT

A low oiling gel filled article comprising a polydiorganosiloxane gel contained within a polysiloxane rubber envelope. The gel is characterized as being the addition product of a first prepolymer having silicon-bonded additional radicals on a terminal silicon atom, and a second prepolymer having silicon-bonded addition radicals on several intermediate silicon atoms. The polydiorganosiloxane prepolymers, and complex fluid, as well as processes for making same, are also disclosed herein.

23 Claims, No Drawings

LOW OILING GEL FILLED ARTICLES, SILOXANE GELS AND LIQUIDS THEREFOR, AND METHODS FOR PRODUCING SAME

BACKGROUND OF THE INVENTION

1. Field of the Invention

The present invention relates to an improved mammary prosthesis for cosmetic augmentation mammoplasty or prosthestic breast restoration following subcutaneous mastectomy. The present invention also relates to siloxane gels and fluids, and methods for producing such gels and fluids.

2. Description of the Prior Art

Since the early 1960's, many silicone elastomeric devices have been successfully used. Silicone devices, either saline filled inflatables or silicone gel filled devices, have become the typical implant in the art. There have been many articles describing the "bleed" or "oiling" which can occur with such devices, these terms relating to the migration of silicone fluids through the outer membrane of the prior art devices. This oiling phenomena is considered undesirable and may cause or contribute to the occurrence of contracture. Contracture occurs when the body chemistry attempts to minimize the surface area of the implant exposed to tissue and forms a sphere of tissue around the implant. This may be considered as a rejection phenomena, may occur excessively in 5–25 percent of all patients.

Prior art devices filled with silicone gel tend to exude silicone fluids of about 200 D.P. (degree of polymerization), typically being trimethyl siloxy end blocked dimethyl siloxanes. In fact, devices including ones currently available may be removed from their sterile package and an oily film is observed on the device and the package. If this oil is blotted onto filter paper and then extracted with xylene and subjected to a gel permeation chromatograph analysis for molecular weight distribution, a curve typical of 1,000 centistoke fluid (200 D.P.) is obtained.

It has been proposed that the reduction of bleed or oiling could be beneficial in that it could eliminate or reduce contracture, or at least contribute to an improved situation in combination with other drugs and/or surgical procedures. One approach in the prior art has been the use of low-bleed devices that seek to provide a low-bleed characteristic by using a polymeric shell that will minimize the diffusion of silicone oils therethrough. This approach is most successful with relatively rigid membranes, which compromise the aesthetic appearance and feel of the device. The more flexible shells, based on other elastomers or silicone copolymers, generally allow the lower molecular weight silicones to migrate. A second approach has been to more completely cross-link the gel, but this typically makes the device much too firm. Also, gel made from higher molecular weight fluid is usually much too sluggish to respond like soft tissue.

A number of mammary prostheses are currently available in the prior art. The Dow-Corning Corporation of Midland, Mich. 48640 markets a Silastic TM brand Mammary Prosthesis, Standard or Low Profile Round Series, under U.S. Pat. No. 3,293,663, issued to Cronin. Other prostheses presently being marketed include one from the McGhan Division of 3M Corporation under the name Intrashiel TM Mammary Implant; the 6,000 Gel-Filled Mammary Prosthesis from the Heyer Shulte Divison of American Hospital and Supply Corporation; and one marketed by the Medical Engineering Corporation under the name Surgitek TM Low Profile Round Gel-Filled Mammary Implant Series 15,000. For all these devices, the prosthesis includes a silicone elastomer shell containing a silicone gel. The shells are relatively thin and have an approximate thickness ranging from 0.005 inches to 0.014 inches.

In contrast to the prosthesis of the present invention, however, the amount of bleed or oiling is higher and the highest and lowest molecular weights of the migratables are considerably lower. Typical figures for a prior art device when tested by compressing the device to cause a twenty percent increase in the diameter of the device for a period of twenty-one hours, followed by sixty-six hours of relaxation to collect the bleed, yields a bleed of about sixty-five milligrams per hundred grams of device, with the lowest molecular weight of about 2,220 and a peak weight of about 14,800 for the migratables. In contrast, a prosthesis constructed in accordance with the present invention, tested under the same conditions, yields a bleed of about fifteen milligrams per hundred grams of device with a lowest molecular weight of about 10,360 and a peak molecular weight of about 25,900 for the migratables.

A number of breast prostheses are disclosed in the patent literature. In U.S. Pat. No. 3,293,663, issued to Cronin on Dec. 27, 1966, there is described a surgically implantable human breast prosthesis. The Cronin patent notes the conventional components for such a prosthesis as including a silicone rubber envelope within which a silicone gel is contained. The Cronin patent also notes the desirability for a soft gel and discusses the measurement of such softness by use of a penetrometer, which uses a ram having a standarized surface area and weight which penetrates to a measured depth after a given time period. A disclosure of another prosthesis using a methyl silicone elastomer contained within a silicone rubber envelope is made in U.S. Pat. No. 3,681,787, issued to Perras on Aug. 8, 1972.

A detailed discussion of the physical considerations and parameters for a mammary prosthesis is contained in the Brill patent, U.S. Pat. No. 4,100,627, issued on July 18, 1978. The Brill patent notes the observation that the typical prior art devices, which include a silicone gel contained within a silicone rubber envelope, permit components of the gel to exude through the silicone rubber. As discussed in the Brill patent, it is consequently desirable to have a combination of silicone gel and rubber which does not result in a significant exudation or oiling of the components of the gel through the rubber envelope. The gel used in the Brill device is the product of methylphenylvinylsiloxy end blocked polydimethysiloxane, dimethylhydrogensiloxy end blocked polydimethylsiloxane, and a polymethylsiloxane cross-linking agent. In contrast to the present invention, the Brill patent does not disclose essentially monofunctional polydiorganosiloxane compounds or their use in the preparation of a complex fluid and gel.

Methods for the preparation of certain organosiloxanes are also disclosed in the prior art. In U.S. Pat. No. Re. 26,697, issued to McVannel on Oct. 28, 1969, there is disclosed a method for polymerizing diorganosiloxane cyclic trimers and diorgano-silethylene cyclic dimers to linear polymers. A similar disclosure is contained in U.S. Pat. No. 3,294,740 issued to McVannel on Dec. 27, 1966. The methods described in these McVannel patents are similar to those preferred in the present invention for the preparation of the first and second polydiorganosiloxane compounds. However, neither of the McVannel patents discloses the preparation thereby of essentially monofunctional compounds of the formulas disclosed and claimed herein. Another disclosure of the polymerization of cyclic polysiloxanes is contained in U.S. Pat. No. 3,337,497, issued to Bostick on Aug. 22, 1967. Alternative methods for the production of polyorganosiloxanes are disclosed in U.S. Pat. No. 3,652,711 issued to Triem on Mar. 28, 1972; U.S. Pat No. 3,183,209, issued to Hartung on May 11, 1965; U.S. Pat. No. 3,037,962, issued to Hartung on June 5, 1962; and U.S. Pat. No. 2,634,284, issued to Hyde on April 7, 1953.

Methods for combining a siloxane compound having a silicon-bonded hydrogen with an unsaturated organic compound are disclosed in U.S. Pat. No. 2,970,150, issued to Bailey on Jan. 31, 1961. In contrast to the present invention, the Baily patent discloses the combination of a siloxane having a silicon-bonded hydrogen to an organic compound not including a silicon atom but including double bonded carbon atoms. The Bailey patent is relevant to the present invention by analogy to the preferred method herein for preparing the complex fluid and gel from the first and second polydiorganosiloxane compounds, since the preferred method involves the addition reaction of the silicon-bonded hydrogens of a first siloxane compound with a double bonded carbon group attached to the second siloxane compound.

Additional examples of siloxane gels are contained in U.S. Pat. No. 4,138,382, issued to Polmanteer on Feb. 6, 1979; and U.S. Pat. No. 3,020,260, issued to Nelson on Feb. 6, 1962. The Polmanteer patent describes a hydrophilic, cross-linked gel produced by the copolymerization of a vinylic constituent with an olefinic hydrolyzable silane containing low molecular weight alkoxy groups. The copolymerization occurs by way of the unsaturated groups, and the material is cross-linked by condensation reaction. The Polmanteer gel is disclosed as useful in a mammary prosthesis. The Nelson patent utilizes a siloxane having a silicon-bonded hydrogen at each end to cross-link an organosiloxane including vinyl groups. The Nelson patent discloses the gel as being useful as a potting or encapsulating material for electronic assemblies, but the Cronin patent previously discussed identifies the Nelson gel as being appropriate for a mammary prosthesis with appropriate adjustment of the gel structure.

SUMMARY OF THE INVENTION

In one aspect the present invention provides novel polydiorganosiloxane compounds which are combined to form a complex fluid, and resulting gel, particularly suited for use in a mammary prosthesis. In related aspects, the present invention provides methods for the preparation of such siloxane materials.

It is an object of the present invention to provide polydiorganosiloxane compounds which are essentially monofunctional and are particularly adapted for the preparation of silicone gels having desired properties.

It is a further object of the present invention to provide a method for the preparation of the complex silicone fluid which is readily cured to a gel particularly suited for use in a mammary prosthesis.

Another object of the present invention is the provision of a complex silicone fluid which is substantially free of lower molecular weight silicone polymers.

It is a further object of the present invention to provide a silicone gel having improved physical properties and characteristics, and in particular being substantially free of lower molecular weight silicone compounds.

A further object of the present invention is to provide a gel filled article which is adapted for use as a mammary prosthesis, and which is characterized by such desirable properties as being low oiling, soft and flexible.

Further objects and advantages of the present invention will become apparent from the description of the preferred embodiment which follows.

DESCRIPTION OF THE PREFERRED EMBODIMENT

For the purposes of promoting an understanding of the principles of the invention, specific language will be used to describe the same. It will nevertheless be understood that no limitation of the scope of the invention is thereby intended, such alterations and further modifications in the invention, and such further applications of the principles of the invention being contemplated as would normally occur to one skilled in the art to which the invention relates.

The present invention provides polysiloxane materials and methods which yield a highly desirable product. These materials and methods are particularly suitable for the production of an implantable mammary prosthesis, but are also suitable for other uses. For the purposes of the present description, the preferred embodiment of the materials and methods will be disclosed with a particular example given for the preparation of an internal mammary prosthesis. It is to be understood, however, that variations of the preferred embodiment are contemplated as indicated herein, with the preferred embodiment being given primarily by way of example.

The present invention relates to a number of components and the product of their combination. As described herein, two distinct polydiorganosiloxane compounds are prepared and are then combined by an addition reaction to form a complex fluid which may be cross-linked to a gel. Certain of the polydiorganosiloxane compounds are essentially monofunctional, meaning that the silicon atoms for the most part include alkyl radicals with a specified number and type of reactive radicals such as silicon-bonded hydrogen and silicon-bonded alkylene radicals. The hydrogen and alkylene radicals provide the desired reactivity for the subsequent addition reaction to combine the siloxane compounds. The term "essentially monofunctional" is used herein to denote the fact that the ready reactivity or functionality of these compounds lies primarily in the silicon-bonded hydrogen or alkylene radicals, although it is of course recognized that as for all compounds other reactivity can be caused to take place. In this regard, the large proportion of organic radicals attached to the silicon atoms, other than the hydrogen and alkylene radicals, are alkyl radicals. In certain embodiments, it is preferred that essentially each of certain of the designated organic radicals be selected from a particular group of alkyl radicals. For the purposes herein, the term "essentially each" is intended to mean that in the length of the polysiloxane chain, at least about seventy-five percent of the designated radical is selected from the specified group. Throughout this description and claims, it is further to be understood that when the term alkyl is used, it is intended that aryl and cycloalkyl groups could be used and are intended thereby.

The first compound of the present invention is an essentially monofunctional polydiorganosiloxane compound having the following formula:

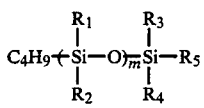

In this compound, $R_1$ and $R_2$ are alkyl radicals preferably having from 1 to about 6 carbon atoms. The letter m designates an integer between about 50 and about 500, and each of the $R_1$ and $R_2$ groups may be independently selected for each of the m groups. Thus, in one of the m groups $R_1$ may be a methyl radical and $R_2$ may be a phenyl radical, and in the next group $R_1$ may be a phenyl radical and $R_2$ an ethyl radical. In this regard, and in similar respects for this invention and the description which follows, it will be appreciated by those skilled in the art that polydiorganosiloxane compounds may include the same or differing organic radicals for the siloxane groups in the chain, primarily depending upon the purity or choice of the materials used to make the compound and also on the method followed for making the compound.

Also for this compound, $R_3$ and $R_4$ are alkyl radicals preferably having from 1 to about 6 carbon atoms, and $R_5$ is selected from the group consisting of: hydrogen and an alkylene radical having from 2 to about 6 carbon atoms. As indicated, the compound is essentially monofunctional with the reactivity being directed to an addition reaction at the site of the $R_5$ compound located on the terminal silicon atom. Preferably the addition reaction is for the addition at a first silicon atom having a hydrogen atom bonded thereto, and a second silicon atom having an alkylene radical bonded thereto. As is well recognized in the art, the addition reaction will result in a connection between these two silicon atoms by an alkyl radical representing the combination of the alkylene radical and the silicon-bonded hydrogen, with the consequent conversion of the double bond in the alkylene radical to a single bond. It is therefore equally suitable that the $R_5$ radical be either a hydrogen or an alkylene radical for participation in the addition reaction.

In a more preferred embodiment, m is an integer between about 160 and about 240. It is also preferred that $R_1$ and $R_2$, and also $R_3$ and $R_4$, are selected from the group consisting of: methyl, ethyl, propyl, phenyl and 3,3,3-trifluoropropyl radicals. Again, $R_1$ and $R_2$ are independently selected for each of the m groups. In a most preferred embodiment, $R_1$, $R_2$, $R_3$ and $R_4$ are methyl radicals, and $R_5$ is a hydrogen atom.

As will be further detailed in the examples, a preferred method for making the first polydiorganosiloxane compound described above involves the polymerization of an appropriate cyclotrisiloxane with butyl lithium. Various cyclotrisiloxanes are well known in the art and may be prepared, for example, by the procedures described in U.S. Pat. No. 2,979,519, issued to Pierce et al. on Apr. 11, 1961. The polymerization steps involving the butyl lithium are well recognized in the art, and therefore the details of the polymerization process will not be further stated herein. It is important to note, however, that an advantage of this polymerization process, and a reason for its being preferred in the present invention, is the fact that polymerization kinetics favor the formation of relatively long, linear polysiloxanes, as opposed to the production of higher molecular weight cyclics as have been prevalent in polymerizations involving the siloxane tetramers. Alternative procedures are disclosed in U.S. Pat. No. 3,294,740 and U.S. Pat. No. Re. 26,697, each issued to McVannel on Dec. 27, 1966 and Oct. 28, 1969, respectively.

The first step then in the preparation of the first polydiorganosiloxane compound is the mixing of the appropriate cylclotrisiloxanes with an effective amount of butyl lithium, accompanied with suitable conditions for the polymerization to occur. There is then added a dialkylchlorosilane to the polymerization product to provide a diorganosilane end group on the polymerized cyclotrisiloxane, with lithium chloride being a by-product. The addition of the dialkylchlorosilane will thereby provide a terminal silicon atom on the first polydiorganosiloxane compound which has two alkyl radicals, and a silicon-bonded hydrogen as the $R_5$ group. As previously indicated, the $R_5$ group may alternatively be an alkylene radical, in which case the appropriate chlorosilane, i.e. a dialkylalkylenechlorosilane, is used to provide the alkylene radical on the terminal silicon atom.

In a particularly preferred embodiment, the $R_1$, $R_2$, $R_3$ and $R_4$ groups of the first compound are methyl radicals and the $R_5$ group is a hydrogen. This compound is readily produced by the polymerization with butyl lithium of hexamethyl cyclotrisiloxane, followed by the addition of dimethyl chlorosilane to the polymerization product to provide the dimethylsilane end group with a hydrogen as the $R_5$ group.

A second compound of the present invention is an essentially polyfunctional polydiorganosiloxane compound having the following formula:

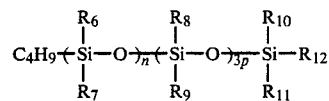

In this compound, $R_6$ and $R_7$ are alkyl radicals having from 1 to about 6 carbon atoms and n is an integer preferably between about 50 and about 400. Each of the $R_6$ and $R_7$ radicals is independently selected for each of the n groups, although they may be, and most preferably are, the same group for each of the n groups. $R_8$ is an alkyl radical having from 1 to about 6 carbon atoms and $R_9$ is an alkylene radical having from 2 to about 6 carbon atoms. The letter p designates an integer from 1 to about 20, with each $R_8$ and $R_9$ group being independently selected for each of the p groups. Further, the n groups and the p groups may be randomly interspersed along the compound chain provided that, as required by the formula, the p groups appear together in multiples of three. $R_{10}$, $R_{11}$ and $R_{12}$ are selected from the group consisting of: hydrogen, an alkylene radical having from 2 to about 6 carbon atoms, and an alkyl radical having from 1 to about 6 carbon atoms.

This second compound is essentially polyfunctional with the functionality arising by the presence of silicon-bonded hydrogen or alkylene radicals. In order to provide a limited number of such addition radicals, the number of siloxane groups having the reactive radicals is kept small in comparison to the other siloxane groups. Thus, there are from three to about 60 of the siloxane groups having the addition radical, but there are between about 50 and about 400 of the siloxane groups containing only alkyl radicals. About 2-5% of reactive radicals to methyl radicals is preferable.

In a related aspect, the terminal silane group may include a reactive radical or may not. If a reactive radical is present on the terminal silicon atom, it is preferable that such radical be consistent with the alkylene radicals present on the intermediate silicon atoms. $R_{10}$, $R_{11}$ and $R_{12}$ are selected from the group consisting of an alkylene radical and an alkyl radical. Most preferably, $R_9$ is a vinyl radical, and it is also preferred that at most one of the $R_{10}$, $R_{11}$, and $R_{12}$ groups be an addition radical, preferably a vinyl radical.

In a particularly preferred embodiment of the second polydiorganosiloxane compound, essentially each $R_6$, $R_7$ and $R_8$ is independently selected, for each of the n and p groups, from the group consisting of: methyl, ethyl, propyl, phenyl and 3,3,3-trifluoropropyl radicals. Similarly it is most preferred that $R_{10}$, $R_{11}$ and $R_{12}$ be selected from the group consisting of: vinyl, methyl, ethyl, propyl, phenyl and 3,3,3-trifluoropropyl radicals. As previously indicated, it is further preferred that only one of these three terminal radicals be an addition radical. The most preferred embodiment of the second compound is one in which essentially each $R_6$, $R_7$ and $R_8$ is a methyl radical, $R_9$ is a vinyl radical, and $R_{10}$, $R_{11}$ and $R_{12}$ are selected from the group consisting of: a vinyl radical and a methyl radical.

Similar to the preferred procedure for making the first polydiorganosiloxane compound, the second such compound is preferably made by the polymerization of cyclotrisiloxanes with butyl lithium. For the second compound, the butyl lithium is used to copolymerize two or more cyclotrisiloxanes, at least one of the cyclotrisiloxanes including a silicon-bonded alkylene radical to provide the addition reactive group at the $R_9$ placement. A variety of appropriate cyclotrisiloxanes could be used in different proportions, depending upon the desired characteristics of the ultimate polymer. Preferably, the cyclics are added in stoichiometric proportions to yield the indicated ratios of the n and p groups. The cyclotrisiloxanes are added together with an effective amount of butyl lithium to provide copolymerization in the manner as previously described with respect to the first compound. Thereafter, the desired chlorosilane is added to the polymerization product to provide a silane end group on the polymerized cyclotrisiloxane.

As indicated with respect to the second compound, the end group may be a trialkyl silane or alternatively may include an alkylene radical within the restrictions previously stated. For a particularly preferred embodiment of the second compound, the compound is prepared by mixing hexamethyl cyclotrisiloxane, 1,3,5-trivinyl, 1,3,5-trimethyl cyclotrisiloxane and an effective amount of butyl lithium to provide copolymerization. The hexamethyl cyclotrisiloxane and butyl lithium should be combined first, and the vinyl-containing siloxane then added thereto, to prevent catalyzing polymerization at the vinyl sites. Thereafter, dimethylvinylchlorosilane is added to the polymerization product to provide a dimethylvinylsilane end group on the polymerized cyclotrisiloxanes. When the $R_9$ groups are hydrogen, an acid catalyzed polymerization must be used.

A third polydiorganosiloxane compound of the present invention comprises a complex fluid having the following formula:

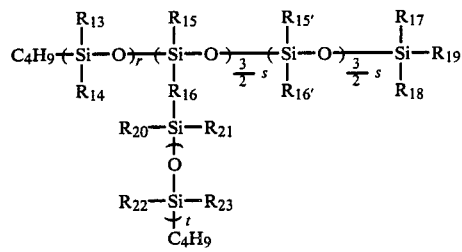

In this third compound, $R_{13}$ and $R_{14}$ are alkyl radicals having from 1 to about 6 carbon atoms. It is intended that alkyl groups may in some instances be replaced by aryl groups. The letter r designates an integer between about 50 and about 400, with each $R_{13}$ and $R_{14}$ group being independently selected for each of the r groups. $R_{15}$ and $R_{15'}$ are alkyl radicals having from 1 to about 6 carbon atoms and $R_{16}$ is an alkyl radical having from about 2 to about 6 carbon atoms. $R_{16'}$ is an alkylene radical having from 2 to about 6 carbon atoms. $R_{20}$, $R_{21}$, $R_{22}$ and $R_{23}$ are alkyl radicals having from 1 to about 6 carbon atoms. The letter t designates an integer between about 50 and about 300, each $R_{22}$ and $R_{23}$ group being independently selected for each of the t groups. The letters s and s' designate an integer from about 1 to about 20, with each of the $R_{15}$, $R_{16}$, $R_{15'}$, $R_{16'}$, $R_{20}$, $R_{21}$, $R_{22}$, and $R_{23}$ groups and t being independently selected for each of the s and s' groups. As will be appreciated in the art, the r, s and s' groups are randomly interspersed along the compound. $R_{17}$, $R_{18}$ and $R_{19}$ are selected from the group consisting of: hydrogen, an alkylene radical having from 2 to about 6 carbon atoms, and an alkyl radical having from 1 to about 6 carbon atoms.

In the third compound, it is preferred that essentially each $R_{13}$, $R_{14}$, $R_{15}$, $R_{20}$, $R_{21}$, $R_{22}$ and $R_{23}$ is independently selected from the group consisting of: methyl, ethyl, propyl, phenyl and 3,3,3-trifluoropropyl radicals, with $R_{16}$ most preferably having two carbons and the others most preferably being methyl radicals. It will further be appreciated that additional carbon or silicon based radicals may be attached to the third compound through one of the indicated silicon-bonded radicals. In particular, one of the $R_{17}$, $R_{18}$ and $R_{19}$ radicals may be an alkyl radical to which a further silicon based polymer may be attached in the manner of the attachment of the silicon based polymer at the $R_{16}$ radical.

In a further method of the present invention, a polydiorganosiloxane material is prepared by the combination of first and second polydiorganosiloxane compounds. A first compound having on a terminal silicon atom a reactive radical selected from the group consisting of hydrogen and an alkylene radical is provided. Also provided is a second such compound having on intermediate silicon atoms several reactive radicals selected from the group consisting of an alkylene radical and hydrogen. Most suitably, the reactive radicals on the second compound are complementary to the reactive radicals of the first compound to provide for the combination of the first and second compounds by an addition reaction. The reactive radicals on one of the first and second compounds are preferably double-bonded carbons and the reactive radicals on the other of the first and second compounds are preferably hydrogens.

The first and second compounds are mixed with a catalytic amount of a compatible platinum catalyst and the mixture is heated to a temperature effective to produce addition reactions between the silicon-bonded hydrogen and alkylene radicals. The addition reaction in the presence of a platinum catalyst, and compatible catalysts for such reactions, are well known in the art and need not be further detailed herein.

The platinum catalyst can be one of those described in U.S. Pat. No. 3,697,473, issued to Polmanteer on Oct. 10, 1972 and which are compatible with the siloxane compositions. Preferable platinum catalysts also include the complexed catalysts described by Willing in U.S. Pat. No. 3,419,593, issued on Dec. 31, 1968. The pertinent parts of the Polmanteer and Willing patents are incorporated herein by reference. The platinum catalyst is used in a catalytic amount, such as greater than about 0.1 and less than about 50 parts by weight of platinum per million parts by weight of siloxane composition. The addition reactions typically will occur at room temperature, or may preferably take place at a temperature of from about 100° to about 200° C. Other conditions may be utilized for the reaction, either in the preparation of the complex fluid or in the later described curing of the fluid to a gel, provided that such conditions do not adversely affect the resulting properties or characteristics of the material. Reactions of a comparable type, though not between two polydiorganosiloxanes as described herein, are described, for example, in U.S. Pat. No. 2,970,150, issued to Bailey on Jan. 31, 1961, and the pertinent portions of such patent are incorporated herein by reference.

This method for preparing a polydiorganosiloxane material is desirably performed by the additive combination of the first and second compounds previously described. In particular, the first compound includes either a hydrogen or an alkylene radical as the $R_5$ group, and the second compound includes either an alkylene radical or hydrogen as the $R_{16}$ group and also perhaps one of the $R_{17}$, $R_{18}$ and $R_{19}$ groups. It is preferred that essentially all of the reactive radicals of the first compound are one of the group consisting of hydrogen and an alkylene radical, and that essentially all of the reactive radicals of the second compound are the other of the group consisting of hydrogen and an alkylene radical.

The portions in which the first and second polydiorganosiloxane compounds are mixed are not critical, and are controlled largely upon the desired characteristics of the resulting complex fluid. It is preferable, however, that the proportions be selected to leave several of the reactive radicals typically from 20 percent to about 80 percent of the original radicals, and preferably about 50 percent, on the second compound intact both to provide the possibility for cross-linking, and also to provide a limit on the nature of the compound structure and therefore of the physical properties of the compound. It is particularly preferred that essentially each of the $R_1$ and $R_2$ groups of the first compound be independently selected, for each of the n groups, from the group consisting of: methyl, ethyl, propyl, phenyl and 3,3,3-trifluoropropyl radicals. It is also most preferred that essentially each of the $R_6$, $R_7$, and $R_8$ groups of the second compound be independently selected, for each of the n and p groups, from the group consisting of: methyl, ethyl, propyl, phenyl, and 3,3,3-trifluoropropyl radicals, and also that the $R_9$ group be a vinyl radical.

In a further aspect of the present invention, the preceding method is further modified to include the added step of cross-linking the complex fluid to form a gel. The cross-linking of the complex fluid typically may be performed in the manner and under the conditions described with respect to the addition reactions forming the complex fluid in the presence of a platinum catalyst. Preferably the appropriate materials are combined just prior to filling the container with the materials, and the curing of the complex fluid to a gel will therefore occur within the container. It is first desirable to wash the complex fluid with a suitable solvent for the free siloxane polymers having a molecular weight of below about 10,000. Typically, the method of producing the complex fluid will result in a number of the first polydiorganosiloxane polymers being present in the fluid but not being attached to a polymer of the type of the second compound. These unattached or "free" polymers are preferably extracted from the fluid to enhance the properties of the fluid. This is suitably accomplished by washing the complex fluid several times with a suitable solvent for these free polymers, such solvents including isopropyl alcohol.

An addition cross-linking agent is then added to the complex fluid and the mixture is cured to a gel. For the purposes herein, the term addition cross-linking agent is intended to mean a compound which will produce a linkage of the third polydiorganosiloxane compounds of the present invention by addition reactions at the remaining silicon-bonded hydrogen or alkylene sites. As previously indicated, it is preferable to produce the complex fluid such that there are several of the addition radicals on the intermediate silicon atoms which remain intact and do not result in the addition of polymers of the type of the first compound to add to the second compound polymer. This may be accomplished or may occur for a variety of reasons including controlled limitations on the reaction time or conditions, stearic hindrances due to the size of the first compound addition at the adjoining radical sites, and control on the proportions of the first and second compounds to be combined.

As described herein, the remaining addition radicals will be either hydrogen or alkylene radicals, and the addition cross-linking agent may be readily determined by those skilled in the art as ones capable of producing an addition reaction with these radicals. In particular, the cross-linking agent may be a silane or siloxane having from 2 to about 200 silicon atoms and having either at least two silicon-bonded hydrogens or two silicon-bonded alkylene radicals, depending upon the nature of the radicals on the complex fluid polymers. A suitable crosslinking agent, for example, is the radical:

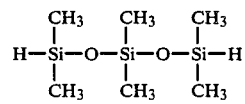

In accordance with known techniques for producing an addition reaction, the complex fluid and cross-linking agent are combined with a catalytic amount of a compatible platinum catalyst and the mixture is cured to a gel. It will further be appreciated by those skilled in the art that the type and amount of cross-linking agent which is added, and the degree of cross-linking which is caused to occur, may be selectively controlled to provide a resulting gel having the desired characteristics.

In a further embodiment of the present invention, there is provided a polydiorganosiloxane gel comprising a cross-linked polymer having the following formula:

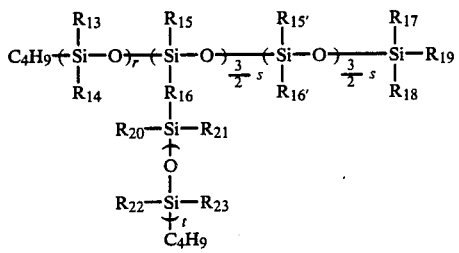

In this gel, the symbols represent the same variables as previously indicated with respect to the third polydiorganosiloxane compound, also described as the complex fluid. It is recognized, however, that the gel may also contain other components to a minor extent. A particularly desirable gel has essentially each $R_{13}$, $R_{14}$, $R_{15}$, $R_{20}$, $R_{21}$, $R_{22}$ and $R_{23}$ independently selected from the group consisting of: methyl, ethyl, propyl, phenyl and 3,3,3-trifluoropropyl radicals, preferably essentially each being methyl radicals.

As for any gel, the polydiorganosiloxane gel of the present invention includes a significant amount of fluid which is entrapped within the cross-linked polymeric structure of the above formula. As is well understood in the art, the proportion of such fluid to the cross-linked structure, by weight, can be readily controlled by a variety of means. For example, the polydiorganosiloxane compound of the complex fluid may be formed to have various numbers of addition radicals per molecule. The type and amount of cross-linking agent, and also the conditions and time limits for cross-linking may be controlled. The degree of cross-linking will also depend on the types of organic radicals present in the compounds of the complex fluid, and the degree of stearic hindrance which will result. Other factors will also affect the degree and nature of the cross-linking, and need not be further described herein as they are well understood in the art.

The manner and the extent to which the cross-linking is limited may be chosen depending upon the properties and characteristics of the resulting gel which are desired. This may be readily determined by experimentation. A particularly preferred composition for this gel is one having from about 10 to about 90 percent fluid, and most preferably about 60 percent of complex fluid by weight entrapped within the gel.

In a related embodiment, a gel filled flexible article is provided which comprises a flexible container within which the described gel is contained. The container should be a relatively tough and flexible, biocompatible envelope. At least a part of the container walls preferably are composed of a polysiloxane rubber and the described gel at least contacts the part of the container wall composed of the rubber. It is preferred that all of the container walls are a polysiloxane rubber, and a rubber based on repeating dimethyl siloxane units is highly desirable. A suitable rubber, for example, is the one sold by the Dow Corning Corp. of Midland, Mich. 48640, under the trademark Q7-2245.

At least a portion of the container walls are composed of a polysiloxane rubber and the silicone gel is in contact with that portion of the walls. It is not necessary that all of the walls be made of the same silicone rubber, although in many instances, particularly in the use of the article as an internal mammary prosthesis, it will be preferred to have all of the container walls comprising the polysiloxane rubber. Apart from these considerations, the design, construction and method of manufacture for the article do not constitute a part of the present invention, and since they are well understood in the art they will not be further detailed herein.

As used herein, the term polysiloxane rubber encompasses a variety of rubbers well known in the art. Silicone rubbers typically comprise a majority of dimethylsiloxane units, but there may also be other diorganosiloxane units such as methylvinylsiloxane units, methylphenylsiloxane units, diphenylsiloxane units, 3,3,3-trifluoropropyl siloxane units and others. The silicone rubber may also include end blocking units such as the triorganosiloxy units, which are well understood in the art and need not be discussed further herein. In addition, the silicone rubber may include other compounds such as fillers, processing aids, additives and pigments, and also may be vulcanized by conventional means such as with organic peroxides, electromagnetic radiation or by use of a polysiloxane cross-linking agent.

The silicone rubber portion of the container walls may comprise any of the above defined silicone rubbers which satisfy the other requirements for the use of the gel filled article. For example, the use of the article as a mammary prosthesis would require that the container walls have a certain degree of toughness, inertness and flexibility. The desired parameters for the physical properties of the container walls may be selected as desired for a given use, and this may be readily accomplished by experimentation, and also by proper selection of the silicone rubber type. Further, the container walls may include two or more layers of silicone rubber to achieve desired results. A particularly preferred construction for the silicone rubber portion of the container walls is a three layer system in which the two outer layers are rubbers composed primarily of dimethylsiloxane units, and the inner layer is rubber composed of diphenyl- and dimethylsiloxane units. This construction yields a rubber of the desired toughness and flexibility, while also including the diphenyldimethylsiloxane rubber which is highly effective in preventing the passage of higher molecular weight components therethrough. The gel of the present invention is advantageous in that it is substantially free of the free, lower molecular weight siloxane compounds, and the use of the gel in combination with this three-layered rubber provides an article which is very low oiling.

It is an important aspect of the present invention that a gel filled article is provided which does not permit significant amounts of the materials in the gel to pass through the container walls. It is of course well accepted that any object placed into the body must be inert, and also must maintain its integrity so as not to interfere with the body components or functions. Most body prostheses are solid and typically have special outer coatings, and the manufacturing process and sterilization techniques will eliminate the possibility of any mobile components passing from the prosthesis to the body. However, it is inherent in the case of a silicone gel filled container having a flexible silicone rubber wall that some of the lower molecular weight components retained in the gel may eventually pass through the container wall into the body. The present invention overcomes this problem in several respects. First, the method for producing the first and second polydiorganosiloxane compounds, and the complex polydiorganosiloxane fluid, results in only a minimum amount of lower molecular weight materials, and these for the most part are eliminated by the purification and cleansing techniques. In addition, the present invention provides a complex fluid which yields a gel having a high degree of softness and pliability with a minimum of the lower molecular weight materials.

In many instances in the prior art, the desired physical properties were achieved by having a gel which included a significant proportion of lower molecular weight materials, in recognition of the fact that the higher the molecular weight is the less soft and less resilient the gel would generally be. In contrast, the complex fluid and gel of the present invention include a polydiorganosiloxane base which includes a number of long chain polymers attached at one end to a primary polymer chain. The primary chains are then cross-linked in the gel but only to a limited extent so that the result is a material of high molecular weight but which has also a high degree of flexibility due to the dangling ends. This form is in distinct contrast to the gels of the prior art which provided a more rigid structure, and therefore required lower molecular weight, non-bound components in order to achieve the same degree of softness and pliability. The non-bound components of the present invention are sufficiently complex to reduce the migration through the shell.

As in any silicon gel, however, there will be a portion of free siloxane polymers. As used herein, the term "free siloxane polymers" refers to those polymers, such as polymers of the form of the first compound, which do not become attached to other polymers in the addition reaction step. These free siloxane polymers will consequently have a much lower molecular weight than the addition reaction products in the complex fluid and in the gel. The free siloxane polymers having a molecular weight of below about 10,000 may be substantially removed by washing the complex fluid with a solvent for the polymers, such as isopropyl alcohol. The removal of these lower molecular weight free polymers is readily accomplished by repeated washings, and as a result there are minimal components in the complex fluid, and conseqent gel, which will migrate through the silicone rubber container walls.

The gel filled article of the present invention is particularly adapted for use as an internal mammary prosthesis. The article may be provided, for example, as a low profile, round design having a range of 110 cc to 350 cc of gel and with a height to diameter ratio of about 1 to 0.10. The polysiloxane rubber preferably has a thickness in the range of 0.003 inches to 0.040 inches, and most suitable is about 0.006 inches in thickness.

The present invention provides novel and advantageous polysiloxane compounds and methods, and in particular provides a gel filled flexible article containing a polysiloxane gel. It is a significant aspect of the present invention that the gel and container combination produce an article which does not have significant bleeding or oiling of the lower molecular weight free polymers through the container walls. In a representative test, the internal mammary prostheses of the prior art were compared with an internal mammary prosthesis constructed in accordance with the present invention. The devices were checked by compressing each device to cause a 20% increase in the diameter of the device for a period of 21 hours, followed by 66 hours of relaxation to collect the bleed. The results for the typical prior art device showed a bleed of about 65 milligrams per hundred grams device, with a lowest molecular weight of about 2,220 and a peak weight of about 14,800 for the migratables. In contrast, the prosthesis constructed in accordance with the present invention showed a bleed of about 15 milligrams per hundred grams of device with a lowest molecule weight of about 10,360 and a peak molecular weight of about 25,900. This comparative test points out two of the significant features of a mammary prosthesis of the present invention. First, the amount of bleed is significantly reduced. Second, the bleed is characterized by comprising higher molecular weight components, indicating a substantial freedom of the gel from the free, lower molecular weight siloxane polymers while achieving the desired physical properties and characteristics.

EXAMPLE 1

An essentially monofunctional first polymer was prepared by loading 1300 grams (5.85 moles) pure hexamethyl cyclotrisiloxane ($Me_2SiO)_3$ into a reaction kettle fitted with a heating mantle, means for stirring, and a dry $N_2$ purge. The trimer was melted and heated, continuing a dry nitrogen purge of about 0.25 cu. ft./hour. When the polymer reached a constant temperature of 90° C., 38.5 ml. n BuLi, 1.6 molar solution (0.062 moles) in hexane (Aldrich Cat. No. 18,617-1) was added along with 21 ml. Diglyme (2-Methoxyethyl ether). Polymerization occurred by evidence of an exotherm to 100° C. and an increased viscosity. The extent of polymerization was followed using Gel Permeation Chromatography.

The polymer was cooled externally using solid $CO_2$ to a temperature of 28° C. 7.0 grams (0.074 moles) dimethyl chlorosilane was added to the reaction kettle to cap the polymer and convert the growing —Si—O—Li endgroup to a —Si—O—S($Me_2$)H endgroup. The dimethyl chlorosilane was allowed to react 3 hours. At the end of this period, 24.8 g bicarbonate (approximately 1 ml. water) was added. The reaction was allowed to continue until alkacid paper indicated neutrality. Filter aid was added and a clear polymer was obtained that had a D.P. of 220 and showed evidence of the presence of unreacted dimethyl trimer and a very small amount of formed dimethyl tetramer.

EXAMPLE 2

A vinyl containing, second polymer was obtained using procedure and equipment similar to that in Example 1, except using the following materials:
1300 grams (5.85 moles) hexamethylcyclotrisiloxane;
149.8 grams (0.58) 1,3,5, trivinyl 1,3,5 trimethyl cyclotrisiloxane;
23.4 ml. diglyme;
48.4 ml. (0.078 moles n-Butyl lithium; and
11.2 grams (0.093 moles) dimethyl vinyl chlorosilane.
In this case, a vinyl endblocked copolymer was prepared. 13 ml. of diglyme was added after the chlorosilane addition to assist the reaction to go to completion. The polymer was neutralized of excess chlorosilane with 62.5 grams sodium bicarbonate and filtered with the aid of Celite ® type filter aid. A degree of polymerization of about 250 was obtained.

EXAMPLE 3

In a separate vessel capable of being heated to 150° C. and purged with dry nitrogen was weighed:
1416.5 grams of a first polymer similar to that of Example 1;
190 grams of a second polymer similar to that of Example 2; and 8 grams H₂PtCl₆.6H₂O solution suitable for catalyzing —SiH H₂C—CHSi— vinyl addition reactions. The mixture was heated at 150° C. until Gel Permeation Chromatography indicated no further reaction. The curves indicated that a large portion of the polymers had reacted to give a highly branched, complex fluid.

EXAMPLE 4

The complex fluid prepared in Example 3 was washed 15 times with isopropyl alcohol. Initial volumes were 1550 ml. polymer and 2200 ml. alcohol. The mixture was stirred vigorously for 30 minutes and the swollen polymer allowed to settle for 30 minutes, giving a swollen polymer lower phase of 3000 cc. The 750 cc. of isopropyl alcohol (with lower molecular weight silicones in solution) was removed and the volume restored to 3750 ml.

This general procedure was repeated 15 times to remove the lower molecular weight cyclics and unreacted linear polymers. The polymer was then stripped of residual 2 propanol using heat and vacuum in a packed column stripper. Gel permeation chrmatography showed that essentially all of the free, unreacted starting materials had been removed. In particular the complex fluid was substantially free of free siloxane compounds having a molecular weight below about 10,000.

EXAMPLE 5

A purified complex fluid similar to that from Example 4 was reacted to form a soft gel by reacting its remaining vinyl groups (or a portion thereof) with an —SiH functional fluid. Specifically, a mixture was made of the following:

440 grams of a polymer similar to that from Example 4;
9.6 grams of a dimethyl siloxane—methyl hydrogen siloxane copolymer containing 0.10% active hydrogen (cross-linking agent); and
7 ppm of a platinum compound capable of catalyzing

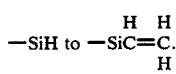

A portion of the mixture was cured to a soft gel by heating in an oven for 3 hours at 150° C. A second portion of the mixture was injected into a thin, 0.007 inch thick membrane, spherical envelope of silicone rubber and cured 3 hours at 150° C. A soft mammary prosthesis resulted which was suitable for implantation. In each instance the gel was found to be substantially free of free siloxane compounds having a molecular weight below about 10,000.

On aging at room conditions for several months, no oily film appeared as with prior art devices. The device was compressed so that the diameter increased 20% for a period of 21 hours. This was followed by 66 hours relaxation to collect "bleed" in an accelerated test on filter paper. Analysis of the silicone oils was performed using Gel Permeation Chromatography. A similar test was performed on a typical prior art device. The results are tabulated below.

| Results | State of the Art Device | Device of Example 5 |
|---|---|---|
| Average amount of bleed, mg. per 100 g. of device (2 tests) | 101 | 9 |

| Results | State of the Art Device | Device of Example 5 |
|---|---|---|
| Molecular Weight: | | |
| Lowest Detected | 2,220 | 10,360 |
| Peak | 14,800 | 25,900 |

EXAMPLE 6

An essentially monofunctional first polymer (monofunctional in vinyl) was prepared by loading 1300 grams (5.85 moles) pure hexamethyl cyclotrisiloxane (Me₂SiO)₃ into a reaction kettle fitted with a heating mantle, means for stirring, and a dry N₂ purge. The trimer was melted and heated, continuing a dry nitrogen purge of about 0.25 cu. ft./hr. When the polymer reached a constant temperature of 90° C., 38.5 ml. n BuLi, 1.6 molar solution (0.062 moles) in hexane (Aldrich Cat. No. 18,617-1) was added along with 21 ml. Diglyme (2-Methoxyethyl ether). Polymerization occurred by evidence of an exotherm to 100° C. and an increased viscosity. The extent of polymerization was followed using Gel Permeation Chromatography.

The polymer was cooled externally using solid CO₂ to a temperature of 28° C. 8.9 grams (0.074 moles) dimethyl vinyl chlorosilane was added to the reaction kettle to cap the polymer and convert the growing —Si—O—Li endgroup to a

endgroup. The dimethyl vinyl chlorosilane was allowed to react 3 hours. At the end of this period, 24.8 g. bicarbonate and approximately 1 ml. water was added. The reaction was allowed to continue until alkacid paper indicated neutrality. Filter aid was added and a clear polymer was obtained that had a D.P. of 210 and showed evidence of the presence of unreacted dimethyl trimer and a very small amount of formed dimethyl tetramer.

EXAMPLE 7

A polyfunctional polymer was prepared by loading 34.8 g. Filtrol 20 (an acid treated clay supplied by Filtrol Corp., Los Angeles, CA) and 700 ml. Toluene into a 3-liter flask fitted with a Dean Stark azeotrope trap, condenser and a suitable means for stirring. The materials were refluxed for about 6 hours to remove the water from the system. About 225 ml. Toluene was removed from the flask through the valve on the Dean Stark water trap.

517.3 g. (7.0 moles) octamethylcyclo tetra siloxane and 45 g. (0.75 moles MeHSiO) of DC 1107 (a methyl hydrogen polymer available from Dow Corning Corporation, Midland, Mich.) were added to the flask. Reflux was continued and Toluene removed until the temperature rose to 140° C.

The polymerization was continued for 3 hours at 140°-144° C. The polymer was cooled, ciltered and stripped of the remaining Toluene, using a moderate temperature, vacuum and a N₂ purge. The resultant polymer had a D.P. of 230 and a hydrogen content of 0.11% (theoretical 0.13%).

EXAMPLE 8

Following examples 3, 4 and 5, the first polymer of Example 6 and the second polymer of Example 7 were processed into silicone gel similar to that demonstrated in Example 5.

What is claimed is:

1. An essentially polyfunctional polydiorganosiloxane compound comprising:

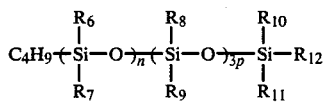

in which:

$R_6$ and $R_7$ are alkyl radicals having from 1 to about 6 carbon atoms;

n is an integer between about 50 and about 400, each $R_6$ and $R_7$ being independently selected for each of the n groups;

$R_8$ is an alkyl radical having from 1 to about 6 carbon atoms;

$R_9$ is an alkylene radical having from 2 to about 6 carbon atoms;

p is an integer from 1 to about 20, each $R_8$ and $R_9$ being independently selected for each of the p groups, the n and p groups being randomly interspersed along the compound provided that the p groups appear together in multiples of 3; and $R_{10}$, $R_{11}$ and $R_{12}$ are selected from the group consisting of: an alkylene radical having from 2 to about 6 carbon atoms, and an alkyl radical having from 1 to about 6 carbon atoms.

2. The compound of claim 1 in which $R_9$ is a vinyl radical.

3. The compound of claim 2 in which essentially each $R_6$, $R_7$ and $R_8$ is independently selected, for each of the n and p groups, from the group consisting of: methyl, ethyl and propyl radicals.

4. The compound of claim 3 in which essentially each $R_6$, $R_7$ and $R_8$ is a methyl radical.

5. The compound of claim 4 in which each of $R_{10}$, $R_{11}$ and $R_{12}$ is selected from the group consisting of: vinyl, methyl, ethyl and propyl radicals.

6. The compound of claim 1 in which essentially each $R_6$, $R_7$ and $R_8$ is independently selected, for each of the n and p groups, from the group consisting of: methyl, ethyl and propyl radicals.

7. The compound of claim 6 in which each of $R_{10}$, $R_{11}$ and $R_{12}$ is selected from the group consisting of: vinyl, methyl, ethyl and propyl radicals.

8. The compound of claim 7 in which essentially each $R_6$, $R_7$ and $R_8$ is a methyl radical, $R_9$ is a vinyl radical, and each of $R_{10}$, $R_{11}$ and $R_{12}$ is selected from the group consisting of: a vinyl radical and a methyl radical.

9. A polydiorganosiloxane compound comprising:

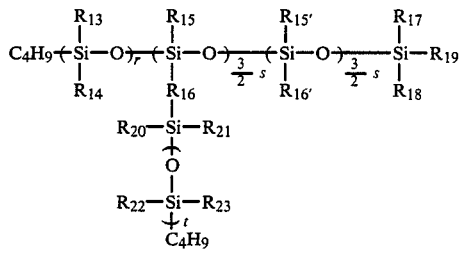

in which:

essentially each $R_{13}$ and $R_{14}$ is an alkyl radical having from 1 to about 6 carbon atoms;

r is an integer between about 50 and about 400, each $R_{13}$ and $R_{14}$ being independently selected for each of the r groups;

$R_{15}$ and $R_{15'}$ are alkyl radicals having from 1 to about 6 carbon atoms;

$R_{16'}$ is a divalent alkyl radical having from about 2 to about 6 carbon atoms;

$R_{16}$, is an alkylene radical having from 2 to about 6 carbon atoms;

$R_{22}$ and $R_{23}$ are alkyl radicals having from 1 to about 6 carbon atoms;

t is an integer between about 50 and about 300, each $R_{22}$ and $R_{23}$ being independently selected for each of the t groups;

$R_{20}$ and $R_{21}$ are alkyl radicals having from 1 to about 6 carbon atoms;

s is an integer from about 1 to about 20, each $R_{15}$, $R_{16}$, $R_{20}$, $R_{21}$, $R_{22}$, $R_{23}$ and t being independently selected for each of the s groups, the r and s groups being randomly interspersed along the compound; and $R_{17}$, $R_{18}$ and $R_{19}$ are selected from the group consisting of: hydrogen, an alkylene radical having from 2 to about 6 carbon atoms, and an alkyl radical having from 1 to about 6 carbon atoms.

10. The compound of claim 9 in which essentially each $R_{13}$, $R_{14}$, $R_{15}$, $R_{20}$, $R_{21}$, $R_{22}$ and $R_{23}$ is independently selected from the group consisting of: methyl, ethyl and propyl radicals.

11. The compound of claim 10 in which essentially each $R_{13}$, $R_{14}$, $R_{15}$, $R_{20}$, $R_{21}$, $R_{22}$ and $R_{23}$ is a methyl radical.

12. The compound of claim 11 in which $R_{16}$ is an ethyl radical and $R_{16'}$ is a vinyl radical.

13. The compound of claim 9 in which essentially each $R_{13}$ and $R_{14}$ is independently selected from the group consisting of: methyl, ethyl and propyl radicals.

14. The compound of claim 9 in which essentially each $R_{15}$ is independently selected from the group consisting of: methyl, ethyl and propyl radicals.

15. The compound of claim 14 in which essentially each $R_{13}$ and $R_{14}$ is independently selected from the group consisting of: methyl, ethyl and propyl radicals.

16. The compound of claim 9 in which essentially each $R_{20}$ and $R_{21}$ is independently selected from the group consisting of: methyl, ethyly and propyl radicals.

17. The compound of claim 9 which essentially each $R_{22}$ and $R_{23}$ is independently selected from the group consisting of: methyl, ethyl and propyl radicals.

18. The compound of claim 17 in which essentially each $R_{20}$ and $R_{21}$ is independently selected from the group consisting of: methyl, ethyl and propyl radicals.

19. A polydiorganosiloxane gel comprising a cross-linked polymer of the formula:

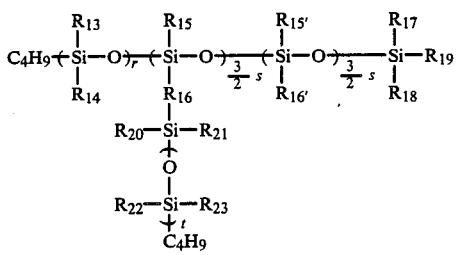

in which:

essentially each $R_{13}$ and $R_{14}$ is an alkyl radical having from 1 to about 6 carbon atoms;

r is an integer between about 50 and about 400, each $R_{13}$ and $R_{14}$ being independently selected for each of the r groups;

$R_{15}$ and $R_{15'}$ are alkyl radicals having from 1 to about 6 carbon atoms;

$R_{16}$ is an alkyl radical having from about 2 to about 6 carbon atoms;

$R_{16'}$ is an alkylene radical having from about 2 to about 6 carbon atoms;

$R_{22}$ and $R_{23}$ are alkyl radicals having from 1 to about 6 carbon atoms;

t is an integer between about 50 and about 300, each $R_{22}$ and $R_{23}$ being independently selected for each of the t groups;

$R_{20}$ and $R_{21}$ are alkyl radicals having from 1 to about 6 carbon atoms;

s and s' are integers from about 1 to about 20, each $R_{15}$, $R_{16}$, $R_{20}$, $R_{21}$, $R_{22}$, $R_{23}$ and t being independently selected for each of the s groups, the r and s groups being randomly interspersed along the compound; and $R_{17}$, $R_{18}$ and $R_{19}$ are selected from the group consisting of: an alkylene radical having from 2 to about 6 carbon atoms, and an alkyl radical having from 1 to about 6 carbon atoms.

20. The gel of claim 19 in which essentially each $R_{13}$, $R_{14}$, $R_{15}$, $R_{20}$, $R_{21}$, $R_{22}$ and $R_{23}$ is independently selected from the group consisting of: methyl, ethyl, propyl, phenyl and 3,3,3-trifluoropropyl radicals.

21. The compound of claim 20 in which essentially each $R_{13}$, $R_{14}$, $R_{15}$, $R_{20}$, $R_{21}$, $R_{22}$ and $R_{23}$ is a methyl radical.

22. The gel of claim 19 in which the polymer is cross-linked with the radical

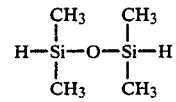

23. The gel of claim 19 and which is substantially free of free siloxane polymers having a molecular weight of below about 10,000.